US009535041B2

(12) United States Patent
Cretin

(10) Patent No.: US 9,535,041 B2
(45) Date of Patent: Jan. 3, 2017

(54) PROPAGATION RATE MEASUREMENT DEVICE, PROPAGATION RATE MEASUREMENT PROGRAM, AND PROPAGATION RATE MEASUREMENT METHOD

(71) Applicant: FURUNO ELECTRIC CO., LTD., Nishinomiya, Hyogo (JP)

(72) Inventor: Dorian Cretin, Nishinomiya (JP)

(73) Assignee: FURUNO ELECTRIC COMPANY LIMITED, Hyogo (JP)

( * ) Notice: Subject to any disclaimer, the term of this patent is extended or adjusted under 35 U.S.C. 154(b) by 236 days.

(21) Appl. No.: 14/401,037

(22) PCT Filed: Apr. 1, 2013

(86) PCT No.: PCT/JP2013/059849
§ 371 (c)(1),
(2) Date: Nov. 13, 2014

(87) PCT Pub. No.: WO2013/175867
PCT Pub. Date: Nov. 28, 2013

(65) Prior Publication Data
US 2015/0122028 A1    May 7, 2015

(30) Foreign Application Priority Data

May 21, 2012  (JP) ................... 2012-115843

(51) Int. Cl.
*G01N 29/07* (2006.01)
*A61B 8/08* (2006.01)
*G01N 29/46* (2006.01)

(52) U.S. Cl.
CPC ............. *G01N 29/07* (2013.01); *A61B 8/0875* (2013.01); *G01N 29/46* (2013.01); *A61B 8/488* (2013.01);
(Continued)

(58) Field of Classification Search
CPC ........ A61B 8/0875; A61B 8/488; G01N 29/46; G01N 29/07; G01N 2291/02483; G01N 2291/103
(Continued)

(56) References Cited

U.S. PATENT DOCUMENTS 4,807,635 A * 2/1989 Ophir ................. A61B 8/00
73/597
5,840,029 A * 11/1998 Mazess ............... A61B 8/0875
600/437

(Continued)

FOREIGN PATENT DOCUMENTS

JP    11-235339 A    8/1999
JP    2010-246692 A    11/2010

OTHER PUBLICATIONS

International Search Report of the corresponding International Application No. PCT/JP2013/059849, dated Jul. 2, 2013.

*Primary Examiner* — J M Saint Surin
(74) *Attorney, Agent, or Firm* — Global IP Counselors, LLP

(57) ABSTRACT

A sonic speed measurement device in which reliability is enhanced while the amount of calculation is minimized is provided. A propagation path postulation component postulates the sonic speed through bone, and calculates propagation paths up until ultrasonic waves transmitted from a wave transmitter are received by oscillators. A postulated propagation time calculator calculates the propagation time it takes for the ultrasonic waves transmitted from the wave transmitter to be received by the oscillators, based on the propagation paths. A Fourier transform component subjects I signals and Q signals of signals outputted by the oscillators to Fourier transform to generate Fourier transform data. A phase shifter shifts the phase of the Fourier transform data for the oscillators in a frequency region according to the
(Continued)

propagation time. A sonic speed derivation component determines the validity of the postulated sonic speed based on the Fourier transform data shifted by the phase shifter.

13 Claims, 5 Drawing Sheets

(52) U.S. Cl.
CPC ............... *G01N 2291/02483* (2013.01); *G01N 2291/103* (2013.01)

(58) Field of Classification Search
USPC .......................................................... 73/597
See application file for complete search history.

(56) References Cited

U.S. PATENT DOCUMENTS

| | | | | |
|---|---|---|---|---|
| 6,328,695 | B1* | 12/2001 | Vammen | A61B 8/0875 600/442 |
| 6,352,512 | B1* | 3/2002 | Wilson | A61B 5/1074 600/449 |
| 7,112,173 | B1* | 9/2006 | Kantorovich | A61B 8/0875 600/438 |
| 2010/0257935 | A1* | 10/2010 | Suetoshi | A61B 8/0875 73/597 |

* cited by examiner

PROPAGATION RATE MEASUREMENT DEVICE, PROPAGATION RATE MEASUREMENT PROGRAM, AND PROPAGATION RATE MEASUREMENT METHOD

CROSS REFERENCE TO RELATED APPLICATIONS

This application is a U.S. National stage of International Application No. PCT/JP2013/059849 filed on Apr. 1, 2013. This application claims priority to Japanese Patent Application No. 2012-115843 filed on May 21, 2012. The entire disclosure of Japanese Patent Application No. 2012-115843 is hereby incorporated herein by reference.

BACKGROUND

Field of the Invention

The present invention relates primarily to the configuration of a sonic speed measurement device that uses ultrasonic waves to measure the sonic speed through a measurement object.

Background Information

There is a known sonic speed measurement device that transmits an ultrasonic wave signal to a measurement object, receives the ultrasonic wave signal that comes back from the measurement object, and derives the sonic speed through the measurement object based on the received ultrasonic wave signal. This type of sonic speed measurement device is discussed in Japanese Laid-Open Patent Application Publication No. 2010-246692 (Patent Literature 1), for example.

The sonic speed measurement device discussed in Patent Literature 1 comprises a plurality of wave receivers. Patent Literature 1 discloses a configuration in which the sonic speed through a measurement object is postulated, the propagation time until ultrasonic waves reach the receivers is calculated based on a postulated sonic speed value, and received signals received by the receivers are shifted by an amount of time corresponding to the propagation time to find an integrated waveform in which the shifted signals have been integrated. In Patent Literature 1, if the postulated sonic speed value is correct, the peaks of the shifted signals reinforce each other, so whether or not the postulated sonic speed value is correct can be determined by examining the integrated waveform. Also, in Patent Literature 1, since the peaks of the received signals received by the receivers do not have to be detected precisely, noise is less likely to have an effect.

SUMMARY

However, a close examination of the configuration of the above-mentioned Patent Literature 1 by the inventors of the present invention revealed the following problems.

With the configuration in Patent Literature 1, processing is performed to shift and integrate received signals received by the wave receivers in the time axis direction. However, since the received signals are digital discrete data, processing to interpolate between data must be performed in order to shift the waveform in the time axis direction at intervals that are shorter than the sampling period. If data interpolation is performed based on a strict theory such as Fourier interpolation in a time domain, the processing takes a long time. It is also possible to give priority to shortening the processing time and use a simple interpolation method such as linear function approximation, but in this case there may be a decrease in the accuracy at which sonic speed is derived.

Also, the configuration in Patent Literature 1 involves finding an integrated waveform by integrating the received signals, so if there is a large amount of data in the received signals, more computation will be required for the integration processing, which is a problem in that the calculation may take a long time. If the calculation takes a long time, the sonic speed cannot be measured smoothly, which puts the operator of this sonic speed measurement device under psychological stress. Also, since this process does not reflect real time well, finding the best measurement location can be difficult, and it may be impossible to perform accurate sonic speed measurement.

The present invention was conceived in light of the above situation, and it is a primary object thereof to provide a sonic speed measurement device that improves reliability while reducing the amount of calculation entailed.

The problem to be solved by the present invention is as discussed above, and the means for solving this problem, and the effect thereof, will now be described.

In a first aspect of the present invention, a propagation rate measurement device with the following configuration is provided. Specifically, this propagation rate measurement device comprises a wave transmitter, a plurality of receivers, a propagation path setting component, a propagation time calculator, a Fourier transform component, a phase shifter, and a propagation rate derivation component. The wave transmitter is configured to transmit signals toward a measurement object. The receivers are configured to receive signals from the measurement object, and are configured to output received signals corresponding to the signals that have been received. The propagation path setting component is configured to set propagation rate of the signals through the measurement object, and is configured to calculate propagation paths up until the ultrasonic waves transmitted from the wave transmitter are received by the receivers. The propagation time calculator is configured to calculate propagation time it takes for the signals transmitted from the wave transmitter to be received by the receivers based on the propagation paths. The Fourier transform component is configured to generate Fourier transform data by subjecting the received signals outputted by the receivers to Fourier transform. The phase shifter is configured to shift phase of the Fourier transform data for the receivers by frequency domain according to the propagation time. The propagation rate derivation component is configured to determine validity of the set propagation rate based on the Fourier transform data that has been shifted by the phase shifter.

Subjecting the signals that have been received to Fourier transform allows processing for shifting the phase of the signals to be performed by frequency domain. With frequency domain, processing for shifting the phase of the signals can be accomplished by simple computation, and almost no errors occur. Therefore, with the above configuration, the derivation of a propagation rate can be carried out very accurately.

The above-mentioned propagation rate measurement device is preferably configured as follows. Specifically, this propagation rate measurement device further comprises an integration processor configured to calculate integrated Fourier transform data by integrating the Fourier transform data of the receivers whose phase has been shifted by the phase shifter by frequency domain. The propagation rate derivation component are further configured to determine the validity of the set propagation rate based on signal intensity of the integrated Fourier transform data.

Thus, the validity of the propagation rate that has been set can be determined by looking at the signal intensity of the integrated Fourier transform data. Also, when the validity of the set propagation rate is determined by frequency domain, there is no need to perform inverse Fourier transform and go back to the time domain, so the calculation load is lighter.

The above-mentioned propagation rate measurement device is preferably configured as follows. Specifically, this propagation rate measurement device further comprises an IQ modulator and a low-pass filter. The IQ modulator is configured to generate I signals and Q signals by the IQ modulation of the signals received by the receivers. The low-pass filter is configured to cut out signals on a high frequency side of the I signals and the Q signals. The Fourier transform component is further configured to subject the I signals and the Q signals to the Fourier transform. The phase shifter is further configured to shift phase of the I signals and the Q signals that have undergone the Fourier transform.

Thus performing IQ modulation allows the original signal spectrum to be moved to the low frequency side, so the low-pass filter can cut out high-frequency waves, leaving only the required signals. Subjecting the I signals and Q signals to Fourier transform allows the processing to be performed by frequency domain.

The above-mentioned propagation rate measurement device preferably further comprises a decimation processor configured to decimate the I signals and the Q signals.

Specifically, the sampling frequency can be dropped from the I signals and Q signals since the low-pass filter cuts out the high-frequency waves. In view of this, decimation can be performed to produce a lighter signal with a smaller data content. This allows processing for shifting the phase with the phase shifter, and integration processing performed by the integration processor to be performed on lighter signals, so the computation load can be greatly reduced.

With the above-mentioned propagation rate measurement device, it is preferable if the integration processor is further configured to integrate the I signals of the receivers that have undergone Fourier transform and whose phase has been shifted, and the Q signals of the receivers that have undergone the Fourier transform and whose phase has been shifted by frequency domain.

Thus integrating the waveforms while still in IQ format in the frequency domain allows the propagation rate to be found without going back to the original signal. This allows computation to be performed while the sampling frequency is still dropped, and reduces the calculation load.

With the above-mentioned propagation rate measurement device, it is preferable if the integration processor is further configured to multiply the I signals of the receivers that have undergone the Fourier transform and whose phase has been shifted, and the Q signals of the receivers that have undergone the Fourier transform and whose phase has been shifted by correction coefficients for correcting amplitude according to the receivers, respectively, and configured to integrate them.

Thus integrating the I signals and Q signals that have undergone the Fourier transform after first correcting according to the receivers allows the intensity of the integrated signal to be accurately evaluated.

In a second aspect of the present invention, a propagation rate measurement program configured as follows is provided. Specifically, this propagation rate measurement program causes a computer to implement a received signal acquisition function, a propagation path setting function, a propagation time calculation function, a Fourier transform function, a phase shift function, and a propagation rate derivation function. With the received signal acquisition function, received signals are acquired from a plurality of receivers that is configured to receive signals transmitted from a wave transmitter toward a measurement object and returned from the measurement object and is configured to output the received signals corresponding to the signals that have been received. With the propagation path setting function, propagation rate of the signals through the measurement object is set, and propagation paths up until the signals transmitted from the wave transmitter are received by the receivers are calculated. With the propagation time calculation function, propagation time it takes for ultrasonic waves transmitted from the wave transmitter to be received by the receivers is calculated based on the propagation paths. With the Fourier transform function, Fourier transform data is generated by subjecting the received signals outputted by the receivers to Fourier transform. The phase shift function shifts phase of the Fourier transform data for the receivers by frequency domain according to the propagation time. With the propagation rate derivation function, validity of the set propagation rate is determined based on the Fourier transform data that has been shifted by the phase shift function.

In a third aspect of the present invention, the following propagation rate measurement method is provided. Specifically, this propagation rate measurement method includes a received signal acquisition step, a propagation path setting step, a propagation time calculation step, a Fourier transform step, a phase shift step, and a propagation rate derivation step. In the received signal acquisition step, received signals are acquired from a plurality of receivers that is configured to receive signals transmitted from a wave transmitter toward a measurement object and returned from the measurement object and is configured to output the received signals corresponding to the signals that have been received. In the propagation path setting step, propagation rate of the signals through the measurement object is set, and propagation paths up until the signals transmitted from the wave transmitter are received by the receivers are calculated. In the propagation time calculation step, propagation time it takes for the signals transmitted from the wave transmitter to be received by the receivers is calculated based on the propagation paths. In the Fourier transform step, Fourier transform data is generated by subjecting the received signals outputted by the receivers to Fourier transform. In the phase shift step, phase of the Fourier transform data for the receivers is shifted by frequency domain according to the propagation time. In the propagation rate derivation step, validity of the set propagation rate is determined based on the Fourier transform data that has been shifted in the phase shift step.

DETAILED DESCRIPTION OF EMBODIMENT

Figure 1:
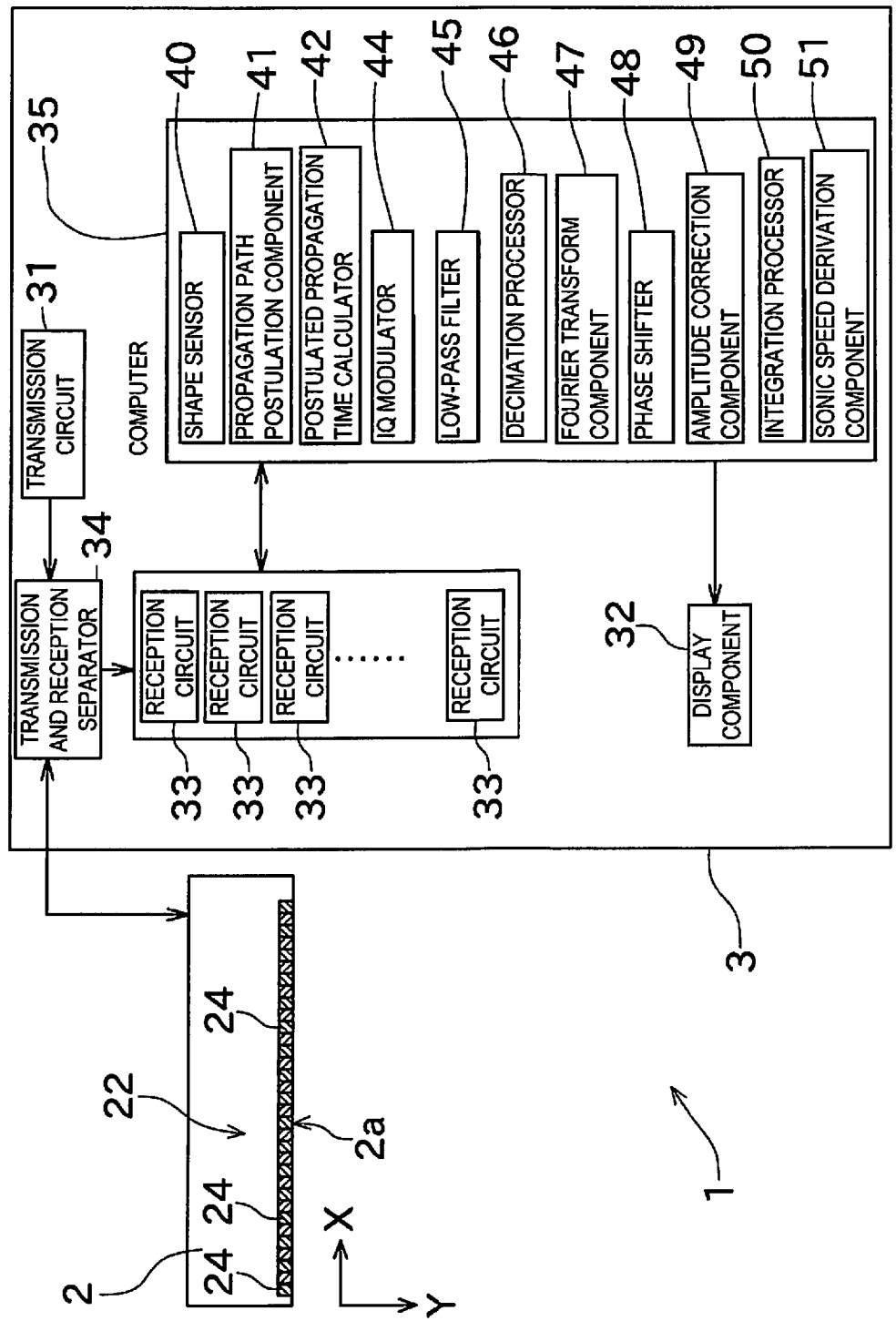
FIG. 1 is a block diagram of an ultrasonic diagnostic device pertaining to an embodiment of the present invention.

An embodiment of the present invention will now be described through reference to the drawings. FIG. 1 is a block diagram of an ultrasonic diagnostic device, serving as the propagation rate measurement device pertaining to an embodiment of the present invention.

The ultrasonic diagnostic device 1 in this embodiment is used for diagnosis in human patients, and in particular uses bone as the measurement object. The ultrasonic diagnostic device 1 in this embodiment functions as a sonic speed measurement device for measuring the sonic speed in bone (the propagation rate of an ultrasonic wave signal) based on an ultrasonic wave signal that has returned from bone. The strength of a bone (an index of the health of the bone) can be derived by measuring the sonic speed in the bone.

As shown in FIG. 1, the ultrasonic diagnostic device 1 is made up of an ultrasonic wave transceiver 2 and a device main body 3.

The ultrasonic wave transceiver 2 send and receives ultrasonic waves. This ultrasonic wave transceiver 2 comprises a contact face 2a that comes into contact with the surface of soft tissue 11 (skin) at the measurement site, and an oscillator array 22. The oscillator array 22 consists of a plurality of oscillators 24 arranged in a single row and spaced equidistantly along the contact face 2a. In the description that follows, the direction in which the oscillators 24 are arranged in the oscillator array 22 will be called the X axis direction.

The oscillators 24 used in this embodiment are ones that generate ultrasonic waves through surface vibration when an electrical signal is applied, and that output an electrical signal (received signal) corresponding to an ultrasonic wave signal upon receiving an ultrasonic wave signal on their surface. Specifically, the oscillators 24 serve as both a wave transmitter and a wave receiver. When it is necessary to distinguish between the plurality of oscillators 24, they will be numbered in the order in which they are arranged, as the oscillator $24_1$, the oscillator $24_2$, . . . , the oscillator $24_n$, . . . the oscillator $24_N$.

The device main body 3 is connected by a cable to the ultrasonic wave transceiver 2, and is configured to be able to send and receive signals to and from the ultrasonic wave transceiver 2. This device main body 3 comprises a transmission circuit 31, a plurality of reception circuits 33, a transmission and reception separator 34, a computer 35, and a display component 32.

The transmission circuit 31 produces an electrical pulse signal for generating ultrasonic waves by vibrating the oscillators 24 of the oscillator array 22, and allows this electrical pulse signal to be applied to the oscillators 24. The center frequency of the electrical pulse signal is about 1 to 10 MHz, for example. A chirp signal may be used, for example, instead of an electrical pulse signal.

After the electrical pulse has been applied, the oscillators 24 vibrate according to this electrical pulse signal. This allows ultrasonic waves to be generated at the oscillators 24. The transmission circuit 31 is configured so that electrical pulse signals can be applied at the desired timing to the plurality of oscillators 24 of the oscillator array 22. This allows the ultrasonic waves to be controlled so that they are sent out all at once or individually from the plurality of oscillators 24.

The plurality of reception circuits 33 are respectively connected to the plurality of oscillators 24 that make up the oscillator array 22. The reception circuits 33 are configured to receive electrical signals (received signals) outputted when the oscillators 24 receive ultrasonic waves, and to produce digital received signals that have undergone amplification, filtering, digital conversion, and other such processing, and send these to the computer 35. The signals directly outputted from the oscillators 24 are analog waveform signals, and the signals transmitted to the computer 35 are digital waveform signals that have undergone signal processing, but in the following description, unless otherwise specified, these will be referred to simply as received signals, without distinguishing between digital and analog waveforms.

The transmission and reception separator 34 is connected between the oscillator array 22 and the transmission circuit 31 and reception circuits 33. This transmission and reception separator 34 prevents the electrical signals (electrical pulse signals) sent from the transmission circuit 31 to the oscillator array 22 from flowing directly to the reception circuits 33, and also prevents the electrical signals sent from the oscillator array 22 to the reception circuits 33 from flowing to the transmission circuit 31 side.

The computer 35 comprises a CPU, a RAM, a ROM, and other such hardware. Software such as the sonic speed measurement program (propagation rate measurement program) pertaining to an embodiment of the present invention is stored in this ROM. This sonic speed measurement program is executed by the above-mentioned hardware to calculate the bone sonic speed at the computer 35.

The operation of the ultrasonic diagnostic device in this embodiment will now be described.

Figure 2A:
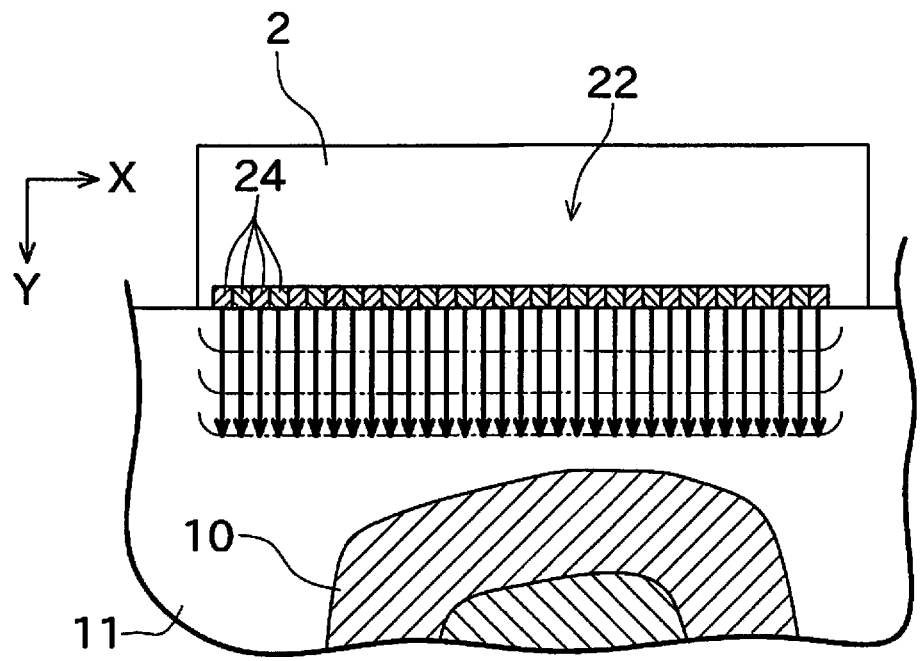
FIG. 2(a) is a simplified diagram of how a plane wave is transmitted to bone.

When diagnosis is performed by this ultrasonic diagnostic device 1, a specific measurement state operation is performed in a state in which the contact face 2a of the ultrasonic wave transceiver 2 has been pressed against the body surface (skin) of the diagnosis subject. When this measurement state operation is performed, the transmission circuit 31 applies electrical pulse signals at the same timing to the oscillators 24 of the oscillator array 22, and as a result a plane wave that moves in a direction perpendicular to the direction in which the oscillators 24 are arranged (the X axis direction) is sent from the oscillator array 22 toward the inside of the body (FIG. 2(a)). The direction in which the plane wave is transmitted from the oscillator array 22 shall be called the Y axis direction.

Figure 2B:
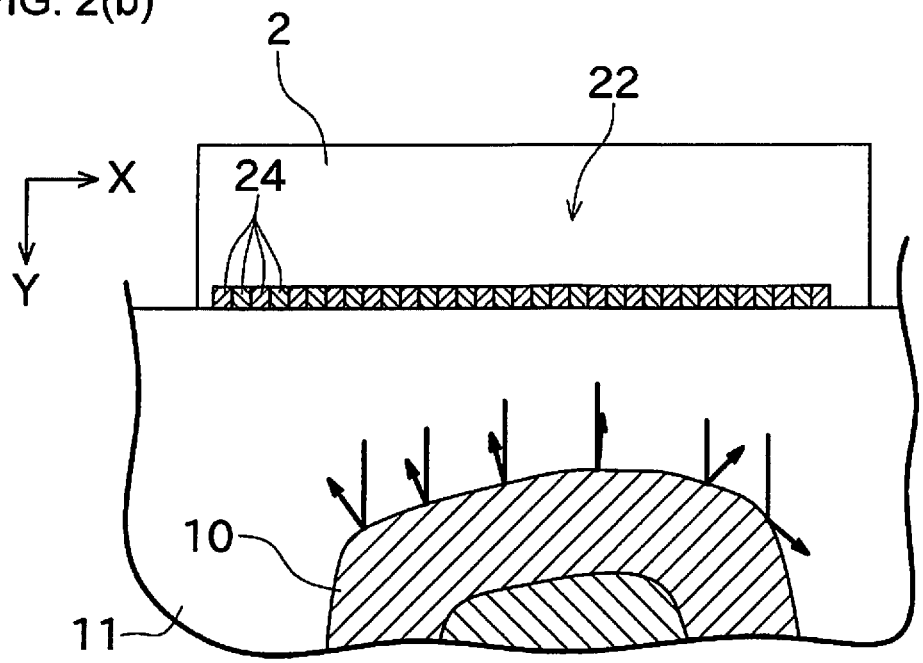
FIG. 2(b) is a simplified diagram of how a reflected wave is produced at the surface of the bone.

The plane wave transmitted from the oscillator array 22 moves through the soft tissue 11 and is reflected at the surface of the bone 10, generating a reflected wave (FIG. 2(b)). This reflected wave is received by at least some of the oscillators 24 out of the plurality of oscillators 24 with which the oscillator array 22 is equipped. The received signals received by the oscillators 24 undergo filtering, sampling, and other such processing as needed by the reception circuits 33, and are thereby converted into digital waveform data. The digital received signals of the oscillators 24 produced by the reception circuits 33 are outputted to the computer 35. The sonic speed measurement program in this embodiment is configured so that the computer 35 implements a received signal acquisition function for acquiring the digital received signals outputted from the reception circuits 33 as discussed above. This allows the computer 35 to process the waveform of the received signals received by the oscillators 24.

The sonic speed measurement program in this embodiment is configured so that the computer 35 implements a shape sensing function of sensing the surface shape of the bone 10 based on the received signals received by the oscillators 24. Therefore, the computer 35 could also be called a shape sensor 40.

Figure 3A:
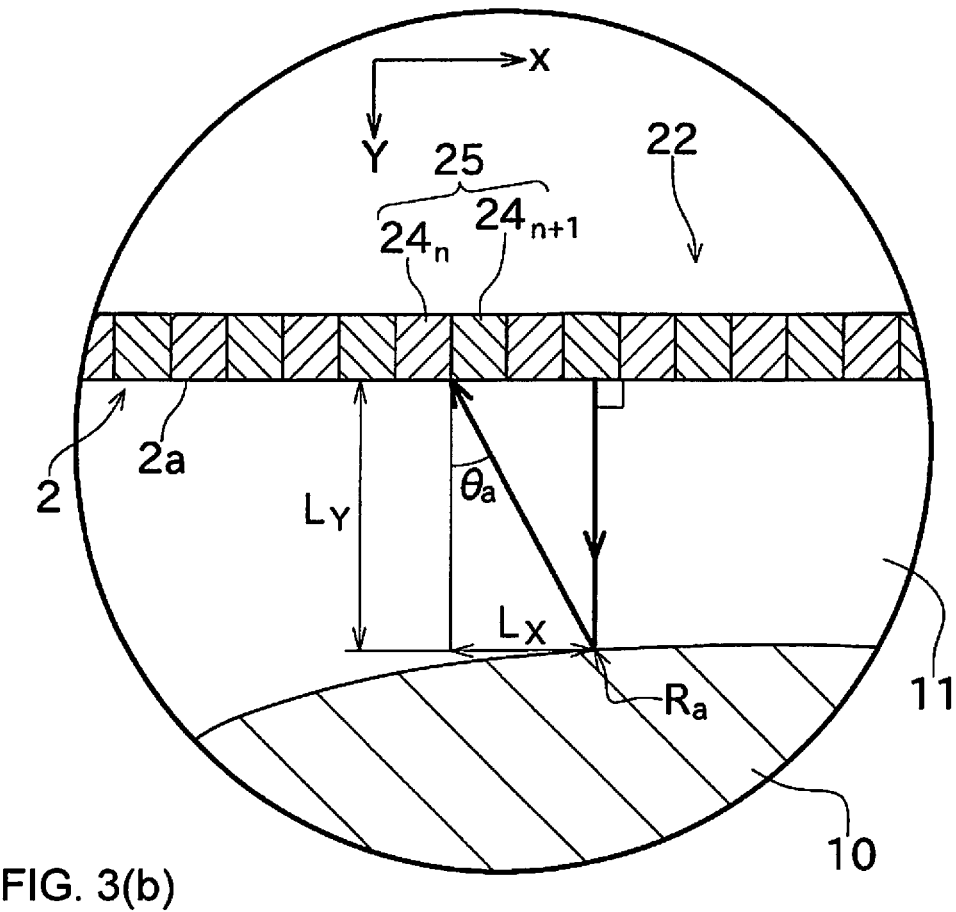
FIG. 3 is a diagram illustrating processing for sensing the shape of a bone surface.
Figure 3B:
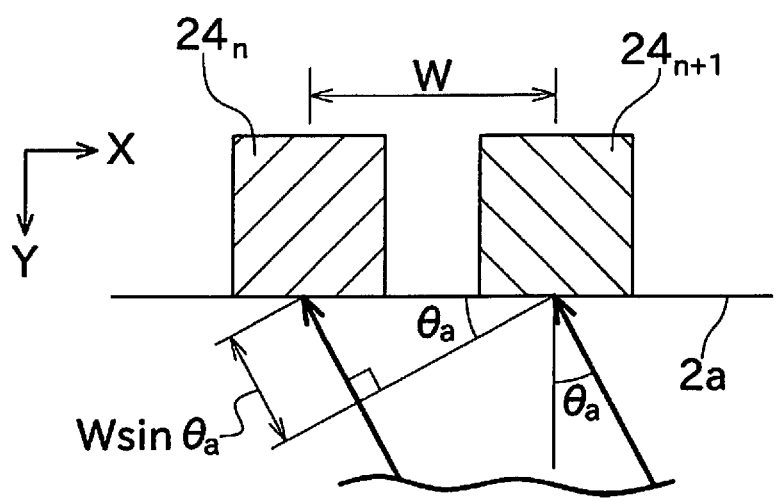

First, the shape sensor 40 identifies two adjacent oscillators out of the plurality of oscillators 24 as an oscillator pair 25. As shown in FIG. 3, let us assume here that a reflected wave from a direction having and angle of $\theta_a$ with respect to the Y axis has arrived at the oscillator pair 25, which consists of the oscillator $24_n$ and the oscillator $24_{n+1}$. If we let W be the spacing between the two oscillators $24_n$ and $24_{n+1}$ (the distance in the X axis direction), as is clear from FIG. 3(b), the reflected wave that arrives at the oscillator $24_n$ (one of the oscillator pair 25) is received after propagating a distance that is longer by $W \sin \theta_a$ than that of the other oscillator $24_{n+1}$. Therefore, the reflected wave is received by the two oscillators at the following time difference.

$$\Delta t = W \sin \theta_a / SOS_{soft}$$

$SOS_{soft}$ here is the speed of sound through the soft tissue 11.

The shape sensor 40 finds the arrival angle $\theta_a$ of the reflected wave with respect to the oscillator pair 25 based on the time difference $\Delta t$ at which the two oscillators $24_n$ and $24_{n+1}$ of the oscillator pair 25 received the reflected wave. Specifically, the arrival angle $\theta_a$ can be found as follows.

$$\theta_a = \text{arc } ?\sin(SOS_{soft} \Delta t / W)$$

In this embodiment, an experimental value is used for the speed of sound $SOS_{soft}$ in the soft tissue 11. However, this is not the only option, and a measured value for the speed of sound in the soft tissue 11 may be used instead.

The shape sensor 40 senses a reflection point $R_a$ of the reflected wave that has reached the oscillator pair 25, based on the arrival angle $\theta_a$ of the reflected wave received by the oscillator pair 25, and the arrival time $T_a$ needed for the reflected wave to arrive at the oscillator pair 25 after the plane wave was transmitted. The arrival time $T_a$ may be the average value for the time from when the plane wave was sent by the oscillator array 22 until the reflected wave arrives at the two oscillators $24_n$ and $24_{n+1}$ constituting the oscillator pair 25. We will let $L_X$ be the distance in the X axis direction from the oscillator pair 25 to the reflection point $R_a$, and let $L_Y$ be the distance in the Y axis direction. As is clear from FIG. 3(a), the propagation distance L of the reflected wave is expressed as follows.

$$L = L_Y + L_Y / \cos \theta_a$$

Meanwhile, if we use the arrival time $T_a$ and the speed of sound $SOS_{soft}$ through the soft tissue 11, we obtain the following:

$$L = SOS_{soft} \times T_a,$$

and therefore the position of the reflection point $R_a$ can be found from the following.

$$L_Y = SOS_{soft} \times T_a \times \cos \theta_a / (1 + \cos \theta_a)$$

$$L_X = L_Y \times \tan \theta_a = SOS_{soft} \times T_a \times \sin \theta_a / (1 + \cos \theta_a)$$

As above, the shape sensor 40 can calculate the position of the reflection point $R_a$ based on the arrival time $T_a$ and the arrival angle $\theta_a$ of the plane wave.

The shape sensor 40 makes up oscillator pairs for all of the oscillators 24 constituting the oscillator array 22, and finds the reflection point $R_a$ in the same way for each oscillator pair. The shape sensor 40 detects a bone surface line by linking the reflection point found as above with a straight line or a curve. The reflection point is a point on the surface of the bone 10, so the bone surface line represents the surface shape of the bone 10. The surface shape of the bone 10 (the bone surface line) can be obtained by the shape sensor 40 as discussed above.

The ultrasonic diagnostic device 1 in this embodiment is configured so derive the bone sonic speed based on the bone surface line found by the shape sensor 40.

The basic concept of the method for deriving the bone sonic speed based on the bone surface line is discussed in Patent Literature 1. In view of this, the configuration of the ultrasonic diagnostic device 1 in this embodiment will first be utilized to describe the basic concept of the Patent Literature 1 in order to facilitate an understanding of the present invention.

Figure 4A:
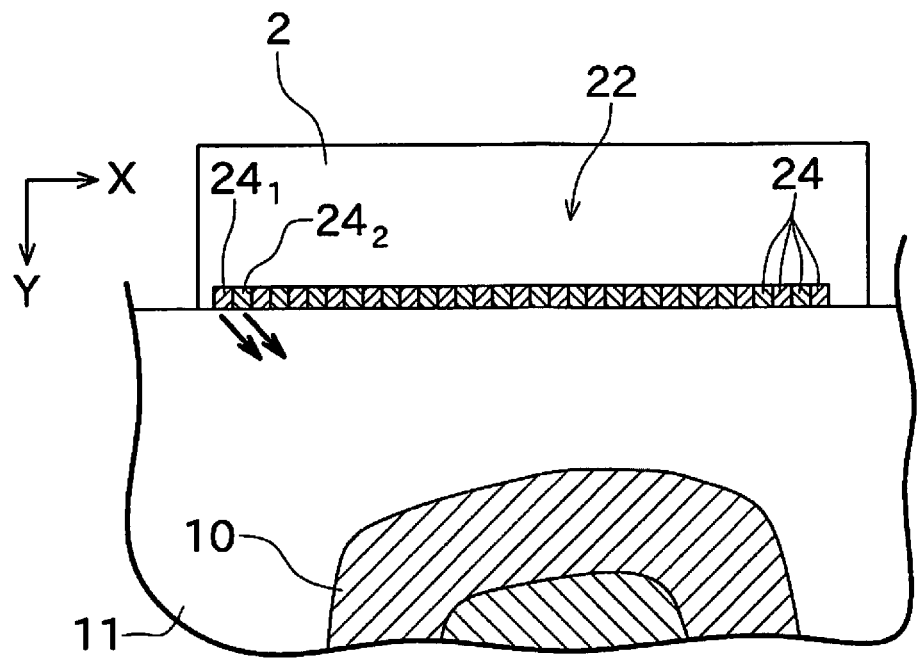
FIG. 4(a) is a simplified diagram of how an ultrasonic wave beam is transmitted to bone.

Once the sensing of the shape of the bone 10 by the shape sensor 40 as described above is finished, the transmission circuit 31 sends an ultrasonic wave beam that is oblique to the bone 10. For example, as shown in FIG. 4(a), an ultrasonic wave beam is transmitted in a direction that is oblique with respect to the Y axis direction by transmitting an ultrasonic wave at shifted timing from two adjacent oscillators (in the case of FIG. 4, the oscillators $24_1$ and $24_2$). In this case, the oscillators $24_1$ and $24_2$ can also be said to serve as transmitters.

Figure 4B:
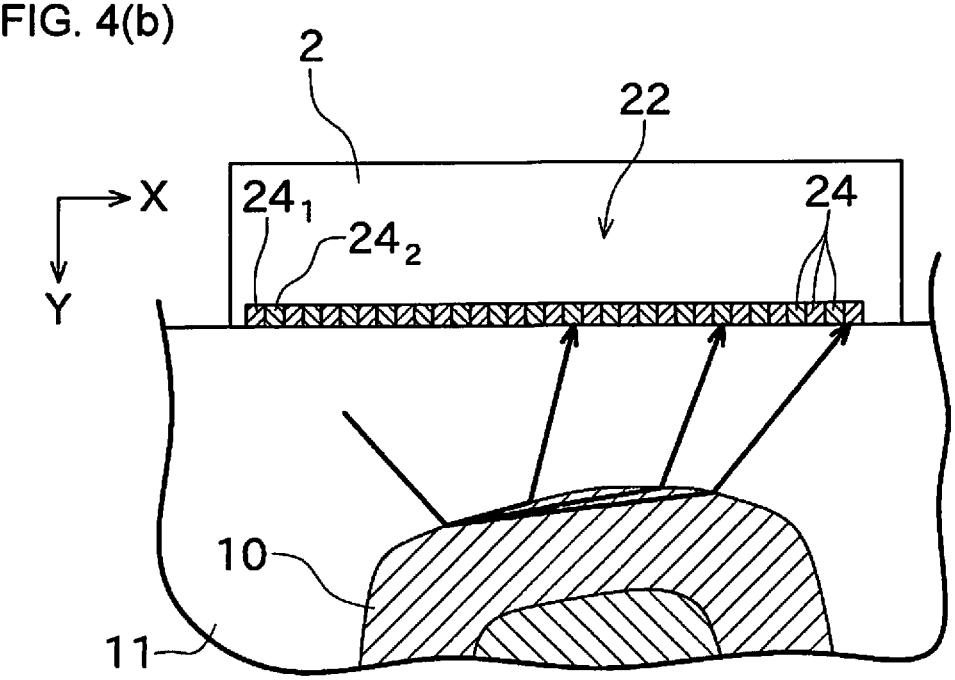
FIG. 4(b) is a simplified diagram of how a surface refracted wave is received by various oscillators.

The ultrasonic wave beam that obliquely hits the surface of the bone 10 is refracted by the surface of the bone 10, and is then incident inside the bone 10. The ultrasonic wave incident in the bone 10 moves through the bone 10 at a different sonic speed than when going through the soft tissue 11. We will let the sonic speed through the bone 10 here be the bone speed of sound $SOS_{bone}$. As shown in FIG. 4(b), if the surface of the bone 10 is curved, an ultrasonic wave that proceeds near the surface of this bone 10 will be refracted again by the surface of the bone 10, and will exit into the soft tissue 11. Thus, an ultrasonic wave that moves through the bone 10 and exits into the soft tissue 11 again is called a surface refracted wave. The surface refracted wave is received by at least some or the oscillators 24 constituting the oscillator array 22. Here, the received signals received by the oscillators $24_1$, $24_2$, etc., shall be called $s_1(t)$, $s_2(t)$, etc., respectively. The received signals $s_1(t)$, $s_2(t)$, etc., of the oscillators 24 are sampled by the reception circuits 33 and converted into digital waveform signals.

The sonic speed measurement program in this embodiment is configured so that the computer 35 implements a propagation path postulation function (propagation path setting function) for postulating the propagation paths of surface refracted waves to the oscillators 24 (setting temporary propagation paths). Therefore, the computer 35 can also be said to be a propagation path postulation component (propagation path setting component) 41.

With the ultrasonic diagnostic device 1 in this embodiment, since the surface shape of the bone 10 (bone surface line) is sensed by the shape sensor 40, the propagation paths of the surface refracted waves with respect to the oscillators 24 can be simply derived by applying Snell's law. To apply Snell's law here, the speed of sound $SOS_{bone}$ in the bone 10 and the speed of sound $SOS_{soft}$ in the soft tissue 11 are needed. As discussed above, the speed of sound $SOS_{soft}$ in the soft tissue 11 can be an experimental value. The bone speed of sound $SOS_{bone}$, however, cannot be known in advance since it is something that the ultrasonic diagnostic device 1 has to calculate.

In view of this, the propagation path postulation component (propagation path setting component) 41 is configured to postulate the bone speed of sound $SOS_{bone}$ (set the temporary bone sonic speed) and calculate the propagation paths. Here, we will let the postulated bone sonic speed be the postulated speed of sound SOS. The propagation path postulation component 41 uses the value set for the postulated speed of sound SOS to apply Snell's law, and thereby calculates the propagation paths of the surface refracted waves with respect to the oscillators 24. The propagation paths calculated here are called postulated propagation paths because they are temporary propagation paths found by postulating the speed of sound SOS.

Also, the sonic speed measurement program in this embodiment is configured so that the computer 35 implements a propagation time calculation function of calculating a postulated value for the propagation time of the surface refracted wave to the oscillators 24. Therefore, the computer 35 can also be said to be a postulated propagation time calculator (propagation time calculator) 42.

The postulated propagation time calculator 42 is configured to find, based on the postulated propagation paths, the propagation time it takes for the oscillators 24 to receive the surface refracted wave after the transmitters (the oscillators 24₁ and 24₂) have sent out an ultrasonic wave beam. The propagation time thus found is a temporary propagation time calculated based on the postulated propagation paths and the postulated speed of sound SOS, so in the following description it is called the postulated propagation time. Here, if we let $t_n$ be the postulated propagation time for the n-th oscillator 24ₙ, this postulated propagation time $t_n$ can be found from the following.

$t_n$=(distance of propagation through soft tissue)×
$SOS_{soft}$+(distance of propagation through bone)
time SOS The distance an ultrasonic wave propagates through soft tissue and the distance it propagates through bone can be found based on the postulated propagation paths calculated by the propagation path postulation component 41.

The surface refracted wave received by the oscillators 24 is received by the oscillators 24 after the propagation time has elapsed since the ultrasonic wave beam is sent out from the transmitters (the oscillators 24₁ and 24₂). Therefore, it is believed that the phases of the waveform of the surface refracted wave received by the oscillators 24 can be brought together on the time axis by shifting the received signals received by the oscillators 24 in the past direction by a time corresponding to the propagation time.

In view of this, the following First Mathematical Formula defines an integrated signal Σs(t), obtained by integrating the received signals $s_1(t)$, $s_2(t)$, etc., of the oscillators 24₁, 24₂, etc., after shifting by the postulated propagation time $t_n$ in the past direction by time domain. Here, $a_n$ is the value of the TVG (time axis vibration correction) for the n-th oscillator 24ₙ.

$$\Sigma s(t) = \sum_n a_n \cdot s_n(t + t_n)$$ [First Mathematical Formula]

When the phase-matched signals are integrated, their waveforms are accentuated, and the signal intensity of the integrated signal Σs is stronger. On the other hand, when signals whose phases are not matched are integrated, their waveforms are weakened, and the signal intensity of the integrated signal Σs is weaker. In the case of the First Mathematical Formula above, when the postulated propagation time $t_n$ postulated for the oscillators 24ₙ matches the actual propagation time, the phases of the various waveforms match up. Since the postulated propagation time $t_n$ of the oscillators 24ₙ is found based on the postulated value for the bone speed of sound (postulated speed of sound SOS), if the postulated speed of sound SOS is corrected (if the postulated speed of sound SOS matches the actual bone speed of sound $SOS_{bone}$, then the phases of the integrated signals will match up best, and the signal intensity of the integrated signal Σs will be highest.

The above is the rough concept behind the sonic speed measurement device disclosed in Patent Literature 1. The sonic speed measurement device disclosed in Patent Literature 1 is configured to find the above-mentioned integrated signal Σs while varying the postulated speed of sound SOS, and to find the relation between the SOS value and the signal intensity of the integrated signal Σs. The sonic speed measurement device discussed in Patent Literature 1 finds the postulated speed of sound SOS at which the integrated signal Σs is maximized, and uses this postulated speed of sound SOS as the measurement value for the bone speed of sound.

Problems encountered with the configuration of the above-mentioned Patent Literature 1 will not be pointed out.

The configuration in Patent Literature 1 was to shift and integrate the received signals $s_n$ received by the oscillators 24ₙ by time domain, so the following two problems were encountered.

The first problem is that since the received signals $s_n$ are digital discrete waveform data, if an attempt is made to shift the received signals $s_n$ in the time axis direction by an interval shorter than the sampling period, processing such as interpolating between data will be required. If interpolation is performed based on a strict theory such as Fourier interpolation in the time domain, the processing takes a long time. If priority is given to shortening the processing time and a simple interpolation method such as linear function approximation is used, the data obtained by interpolation between data by linear function approximation will be nothing but an approximation, and error will inevitably occur.

The second problem is that since the integrated signal Σs has to be found by adding up the data for the various received signals $s_n$ one at a time, many computations are required, making real-time processing difficult. The amount of data of the received signals $s_n$ depends on the sampling frequency of the received signals $s_n$. The higher is the sampling frequency, the more data there will be, and the greater the calculation load. One way to reduce the calculation load is to lower the sampling frequency of the received signals $s_n$, but this ends up reducing the reliability of the waveform data.

As a result of close scrutiny of the above problems, the inventors discovered that they can be solved by performing the processing of the First Mathematical Formula (shifting and integrating the received signals) by frequency domain, which led to the perfection of the present invention. The characteristic features of the present invention will now be described.

The First Mathematical Formula becomes the following Second Mathematical Formula in frequency domain. $S_n(\omega)$ is the frequency domain expression of the received signals $s_n(t)$ (after the Fourier transform of the received signals $s_n(t)$). ΣS in the Second Mathematical Formula shall be called integrated Fourier transform data. j in the formula is an imaginary unit.

$$\sum S(\omega) = \sum_n a_n \cdot S_n(\omega) \cdot e^{j\omega t_n}$$ [Second Mathematical Formula]

The processing of the First Mathematical Formula in which the received signals $s_n(t)$ have been shifted in the past direction by the propagation time $t_n$ can be accomplished by simply processing involving the multiplication of $e^{j\omega t n}$ in the frequency domain. Consequently, processing for interpolating between data, such as when the received signals are shifted in time domain, is unnecessary. Therefore, no occur is caused by interpolation between data, so more accurate sonic speed derivation is possible. That is, the first problem mentioned above can be solved by performing processing of shifting the phase of received signals by frequency domain.

Also, the processing of the Second Mathematical Formula (multiplication by $e^{j\omega t n}$) can be performed at a constant accuracy, regardless of the sampling frequency of the received signals $s_n$. That is, when the above-mentioned processing is performed by frequency domain, the sampling frequency of the received signals $s_n$ need not be that high. Accordingly, the amount of data is smaller and fewer computations are needed, so processing in real time is possible. Also, the processing involving multiplication by $e^{j\omega t n}$ can be accomplished more simply than with processing involving interpolation between data, so the computation load can be reduced in this respect as well. That is, the second problem mentioned above can be solved by performing the processing of "shifting and integrating the received signals" by frequency domain.

The sonic speed measurement method used in the ultrasonic diagnostic device 1 in this embodiment will now be described in specific terms through reference to the flowchart in FIG. 5.

First, the ultrasonic diagnostic device 1 sends an ultrasonic wave beam from transmitters (such as the $24_1$ and $24_2$) toward the bone 10, at an angle to the Y axis (step S101). This ultrasonic wave beam is refracted by the surface of the bone 10, is incident in the interior of the bone 10, is again refracted by the bone surface, exits into the soft tissue 11, and is received by the oscillators 24 (step S102, received signal acquisition step).

The received signals received by the oscillators $24_1$, $24_2$, etc., shall be called $s_1(t)$, $s_2(t)$, etc., respectively. The received signals $s_1(t)$, $s_2(t)$, etc., of the oscillators 24 are sampled by the reception circuits 33 and converted into digital waveform signals. The sampling frequency here shall be termed $fs_H$.

The sonic speed measurement program in this embodiment is configured so that the computer 35 implements an IQ modulation function of subjecting the received signals received by the oscillators 24 to IQ modulation. Therefore, the computer 35 can also be called an IQ modulator 44.

The IQ modulator 44 performs known IQ modulation on the received signals $s_1(t)$, $s_2(t)$, etc., received by the oscillators $24_1$, $24_2$, etc., thereby obtaining I signals and Q signals for the received signals. As is well known, this IQ modulation produces I signals by mixing a reference signal of a modulated frequency with a certain modulated signal, and Q signals by mixing signals whose phase has been shifted by 90° from the reference signal. Specifically, the IQ modulator 44 subjects the received signals $s_n(t)$ received by the oscillators 24 to IQ modulation according to the following formula, thereby producing I signals $i_n(t)$ and Q signals $q_n(t)$ (step S103).

$$i_n(t)=s_n(t)\cdot\cos(\omega_0 t)$$

$$q_n(t)=s_n(t)\cdot\sin(\omega_0 t) \quad \text{[Third Mathematical Formula]}$$

In the Third Mathematical Formula above, $\omega_0$ is the angular frequency representation of a modulation frequency $f_0$ of the ultrasonic wave beam sent by the transmitter toward the bone 10 ($\omega_0=2\pi f_0$).

As is well known, the spectrum of a certain modulated signal can be moved to the low frequency side by mixing a signal of a modulated frequency with the modulated signal. That is, the I signals and Q signals produced by the IQ modulator 44 have their signal spectra moved to the low frequency side. The sonic speed measurement program in this embodiment is configured so that the computer 35 implements a low-pass filter function of subjecting I signals and Q signals to low-pass filtering. Therefore, the computer 35 can also be called a low-pass filter 45. Since the spectrum of useful information has moved to the low frequency side, even though signals on the high frequency side are cut out, there is almost no deterioration in the information had by the original received signals $s_n$.

The low-pass filter 45 subjects the I signals $i_n(t)$ and Q signals $q_n(t)$ of the oscillators 24 to low-pass filtering, which cuts out frequencies higher than the modulated frequency $f_0$, leaving just the spectrum on the low frequency side (the base band) (step S104).

As discussed above, when the high frequency side of the I signals $i_n(t)$ and Q signals $q_n(t)$ is cut out, the Nyquist frequency needed to express the information of the I signals $i_n(t)$ and Q signals $q_n(t)$ will be lower, so it is possible to lower the sampling frequency. In view of this, the sonic speed measurement program in this embodiment is configured so that the computer 35 implements a decimation processing function of decimating the I signals and Q signals from which the high frequencies have been cut out. Therefore, the computer 35 can also be called a decimation processor 46.

The decimation processor 46 performs decimation of the I signals $i_n(t)$ and Q signals $q_n(t)$ of the oscillators 24 from which the high frequencies have been cut out by the low-pass filter 45 (step S105). The term decimation here means processing to lower the sampling frequency of a digital waveform. Decimation by time domain can be accomplished by thinning out the data of the I signals $i_n(t)$ and Q signals $q_n(t)$ at regular intervals. This produces I signals $i_n(t)$ and Q signals $q_n(t)$ in which the sampling frequency has been dropped. We shall let $fs_L$ be the sampling frequency after decimation.

Performing decimation reduces the amount of data of the I signals $i_n(t)$ and Q signals $q_n(t)$ and results in lighter data. Thus reducing the amount of data means that there will be fewer computations for the I signals $i_n(t)$ and Q signals $q_n(t)$ in subsequent steps, so the computation load can be greatly reduced.

To perform the computation of the Second Mathematical Formula, a frequency domain representation $S_n(\omega)$ of the received signal $s_n(t)$ is necessary. The received signal $s_n(t)$ can be represented by the following Fourth Mathematical Formula when the I signals $i_n(t)$ and Q signals $q_n(t)$ are used.

$$s_n(t)=\{i_n(t)+j\cdot q_n(t)\}e^{-j\omega_0 t} \quad \text{[Fourth Mathematical Formula]}$$

With the ultrasonic diagnostic device 1 in this embodiment, however, since the sampling frequency is lowered by performing decimation of the I signals $i_n(t)$ and Q signals $q_n(t)$, the sampling frequency will be too low to reproduce the original received signal $s_n(t)$. Specifically, in this embodiment, the original received signal $s_n(t)$ cannot be fully restored by the Fourth Mathematical Formula. In view of this, the same computation as in the Second Mathematical Formula can be implemented until representation by the I signals $i_n(t)$ and Q signals $q_n(t)$ is achieved, without restoring the original received signal $s_n(t)$ (without performing the computation of the Fourth Mathematical Formula).

First, the phase-shifted Fourier transform data $s_n(\omega)$ of the oscillators $24_n$ is defined by the following Fifth Mathematical Formula. $I_n(\omega)$ is the frequency domain representation of the I signal $i_n(t)$, and $Q_n(\omega)$ is the frequency domain representation of the Q signal $q_n(t)$. The correction coefficient $\alpha_n$ is a coefficient for correcting the signal level of the signals received by the oscillators $24_n$, and is determined by taking into account the TVG values of the oscillators $24_n$, the postulated propagation time $t_n$ of the surface refracted wave for the oscillators $24_n$, and so forth.

$$s_n(\omega) = \alpha_n \cdot I_n(\omega) e^{j\omega t_n} + j \cdot \alpha_n Q_n(\omega) e^{j\omega t_n} \quad \text{[Fourth Mathematical Formula]}$$

The integrated Fourier transform data $\Sigma S$ obtained by integrating the phase-shifted Fourier transform data $s_n(\omega)$ of the oscillators $24_n$ is defined by the following Sixth Mathematical Formula. Thus, the integrated Fourier transform data $\Sigma S$ can be calculated based on the I signals $i_n(\omega)$ and Q signals $q_n(\omega)$ of the frequency domain, without restoring the original received signal $s_n(t)$.

$$\Sigma S(\omega) = \sum_n s_n(\omega) \quad \text{[Sixth Mathematical Formula]}$$

The integrated Fourier transform data $\Sigma S$ defined by the Sixth Mathematical Formula can be thought of as the integrated signal $\Sigma s$ of the First Mathematical Formula being represented by frequency domain. As already described, if the postulated speed of sound SOS postulated by the propagation path postulation component 41 is correct, then the signal intensity of the integrated signal $\Sigma s$ will be at its maximum. Therefore, if the integrated Fourier transform data $\Sigma S$ that is a frequency domain representation of this integrated signal $\Sigma s$ also has the correct postulated speed of sound SOS, then its signal intensity will be at its maximum. Thus, the signal intensity of the integrated Fourier transform data $\Sigma S$ can be said to be an index for determining the validity of the postulated speed of sound SOS by frequency domain.

To calculate the integrated Fourier transform data $\Sigma S$ from the Fifth and Sixth Mathematical Formulas, the ultrasonic diagnostic device 1 in this embodiment subjects the I signals $i_n(t)$ and Q signals $q_n(t)$ of the oscillators 24, to Fourier transform, and thereby finds the frequency domain representations $I_n(\omega)$ and $Q_n(\omega)$, and also finds the phase-shifted Fourier transform data $s_n(\omega)$ from the Fifth Mathematical Formula based on this. Once the phase-shifted Fourier transform data $s_n(\omega)$ is found for the oscillators $24_n$, this data can be integrated to calculate the integrated Fourier transform data $\Sigma S$.

Figure 5:
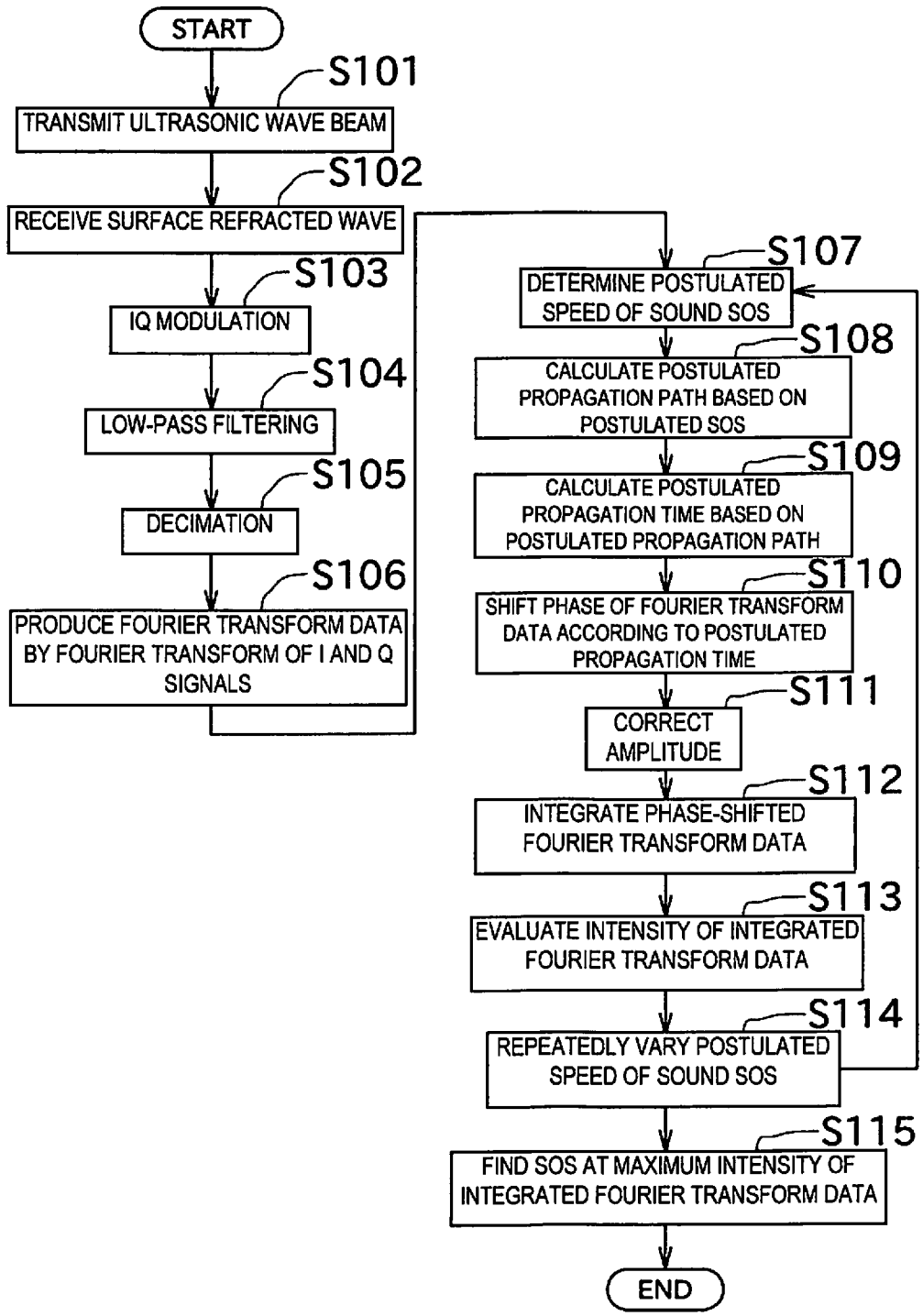
FIG. 5 is a flowchart of the sonic speed measurement method pertaining to this embodiment.

With the above points in mind, the description of the sonic speed measurement method pertaining to the ultrasonic diagnostic device 1 of the present invention will now be continued, again through reference to the flowchart in FIG. 5.

The sonic speed measurement program in this embodiment is configured to that the computer 35 implements a Fourier transform function of subjecting I signals and Q signals to Fourier transform. Therefore, the computer 35 can also be said to be a Fourier transform component 47.

The Fourier transform component 47 subjects the I signals $i_n(t)$ and the Q signals $q_n(t)$ of each oscillator 24 from which the amount of data has been reduced by the decimation processor 46 to fast Fourier transform (FFT), which produces Fourier transform data $I_n(\omega)$ and $Q_n(\omega)$ (step S106; Fourier transform step). In this embodiment, the I signals $i_n(t)$ and the Q signals $q_n(t)$ have their sampling frequency lowered by the decimation processor 46, so Fourier transform data $I_n(\omega)$ and $Q_n(\omega)$ obtained by subjecting these signals to Fourier transform also become lighter data with a smaller data quantity.

The propagation path postulation component 41 then sets the postulated speed of sound SOS (the postulated speed of sound through bone; step S107), and calculates the postulated propagation paths of the surface refracted waves to the oscillators $24_n$ based on this postulated speed of sound SOS (step S108). Also, the postulated propagation time calculator 42 calculates the postulated propagation time $t_n$ of the surface refracted wave of the oscillators $24_n$ (step S109). The method for calculating the postulated propagation time $t_n$ by postulating the bone speed of sound has already been described, and so will not be described again here.

The sonic speed measurement program in this embodiment is configured so that the computer 35 implements a phase shift function of shifting the phase of the Fourier transform data $I_n(\omega)$ and $Q_n(\omega)$ of the oscillators $24_n$ according to the postulated propagation time $t_n$. Therefore, the computer 35 can also be said to be a phase shifter 48.

In frequency domain, processing to shift the phase of a signal according to the postulated propagation time $t_0$ can be implemented by processing to multiply $e^{j\omega t_n}$. The phase shifter 48 multiplies the $e^{j\omega t_n}$ by the Fourier transform data $I_n(\omega)$ and $Q_n(\omega)$ of the oscillators $24_n$ to produce phase-shifted Fourier transform data $I_n(\omega)e^{j\omega t_n}$ and $Q_n(\omega)e^{j\omega t_n}$ (step S110; phase shifting step). As discussed above, since the Fourier transform data $I_n(\omega)$ and $Q_n(\omega)$ are lighter data with a smaller data quantity, fewer computations are required for processing to shift the phase of the Fourier transform data $I_n(\omega)$ and $Q_n(\omega)$, which lessens the calculation burden.

In frequency domain, the processing to shift the phase of a signal (processing to multiply $e^{j\omega t_n}$) can be performed at a consistent accuracy, regardless of the sampling frequency of the Fourier transform data $I_n(\omega)$ and $Q_n(\omega)$. Thus, in this embodiment, since the processing to shift the phase of the signals is performed by frequency domain, there will be no increase in error even when shifting the phase of I signals and Q signals whose sampling frequency has been lowered by decimation.

The sonic speed measurement program in this embodiment is configured so that the computer 35 implements an amplitude correction function of correcting the amplitude of the Fourier transform data whose phase has been shifted by the phase shifter 48. Therefore, the computer 35 can also be said to be an amplitude correction component 49. The amplitude correction component 49 multiplies the phase-shifted Fourier transform data $I_n(\omega)e^{j\omega t_n}$ and $Q_n(\omega) e^{j\omega t_n}$ of the oscillators $24_n$ by a correction coefficient $\alpha_n$, thereby producing amplitude-corrected Fourier transform data $\alpha_n I_n(\omega) e^{j\omega t_n}$ and $\alpha_n Q_n(\omega)e^{j\omega t_n}$ (step S111). This allows the Fourier transform data $I_n(\omega)$ and $Q_n(\omega)$ of the oscillators $24_n$ to be corrected according to the TVG values of the oscillators $24_n$ and to the postulated propagation time $t_0$ of the surface refracted wave for those oscillators $24_n$. As discussed above, since the Fourier transform data $I_n(\omega)$ and $Q_n(\omega)$ are lighter data with a smaller data quantity, fewer computations are required for processing to correct the amplitude of the Fourier transform data $I_n(\omega)$ and $Q_n(\omega)$, which lessens the calculation burden.

The sonic speed measurement program in this embodiment is configured so that the computer implements an integration processing function of integrating the phase-shifted Fourier transform data $s_n(\omega)$ of the oscillators. Therefore, the computer 35 can also be said to be an integration processor 50.

First, the integration processor 50 plugs the amplitude-corrected Fourier transform data $\alpha_n I_n(\omega)e^{j\omega t n}$ and $\alpha_n Q_n(\omega) e^{j\omega t n}$ of the oscillators $24_n$ produced by the amplitude correction component 49 into the Fifth Mathematical Formula to produce the phase-shifted Fourier transform data $s_n(\omega)$ of the oscillators $24_n$. As discussed above, since the Fourier transform data $I_n(\omega)$ and $Q_n(\omega)$ are lighter data with a smaller data quantity, the phase-shifted Fourier transform data $s_n(\omega)$ is also lighter data with a smaller data quantity.

The integration processor 50 then integrates the phase-shifted Fourier transform data $s_n(\omega)$ of the oscillators $24n$ by frequency domain, thereby calculating the integrated Fourier transform data $\Sigma S$ defined by the Sixth Mathematical Formula (step S112). As discussed above, since the phase-shifted Fourier transform data $s_n(\omega)$ is lighter data with a smaller data quantity, fewer computations are required for processing to integrate the sets of phase-shifted Fourier transform data $s_n(\omega)$, which lessens the calculation burden.

The sonic speed measurement program in this embodiment is configured so that the computer 35 implements a sonic speed derivation function (propagation rate derivation function) of finding the correct speed of sound by determining the validity of the postulated speed of sound SOS based on the integrated Fourier transform data $\Sigma S$ found by the integration processor 50. Therefore, the computer 35 can also be said to be a sonic speed derivation component (propagation rate derivation component) 51.

The sonic speed derivation component 51 is configured to evaluate the signal intensity of the integrated Fourier transform data $\Sigma S$ found by the integration processor 50 (step S113). An example of how the signal intensity of the integrated Fourier transform data $\Sigma S$ is evaluated is a method in which an intensity evaluation value V is found, as defined in the Seventh Mathematical Formula. The intensity evaluation value V shown in the Seventh Mathematical Formula is the sum of the intensities over a spectrum at various angular frequencies of the integrated Fourier transform data $\Sigma S$. The Gothic German R here is a symbol expressing a real number component, and the Gothic German I is a symbol expressing an imaginary number component.

[Seventh Mathematical Formula]

$$V(\Sigma S) = \sum_{\omega} \sqrt{(I'(\omega))^2 + (Q'(\omega))^2}$$

$$I'(\omega) = \mathfrak{R}(\Sigma S(\omega))$$

$$Q'(\omega) = \mathfrak{I}(\Sigma S(\omega))$$

The sonic speed derivation component 51 in this embodiment is configured to find the postulated speed of sound SOS at which the intensity evaluation value V is maximized. More specifically, the sonic speed derivation component 51 repeatedly performs processing to find the intensity evaluation value V while successively varying the postulated speed of sound SOS (a loop from step S107 to step S114). This finds the relation between the postulated speed of sound SOS and the intensity evaluation value V, so the postulated speed of sound SOS at which the intensity evaluation value V is maximized can be found. The postulated speed of sound SOS when the intensity evaluation value V is at its maximum expresses the actual bone speed of sound. The sonic speed derivation component 51 senses the postulated speed of sound SOS at which the intensity evaluation value V is maximized, and employs this postulated speed of sound SOS as the measured value of the speed of sound (step S115; sonic speed derivation step). The above processing allows the speed of sound through the bone 10 to be derived.

The integrated Fourier transform data $\Sigma S$ and the intensity evaluation value V can be calculated while still in the frequency domain. This allows the validity of the postulated speed of sound SOS to be determined without returning to the time domain by performing inverse Fourier transform. Thus, the configuration of this embodiment does not require processing to return to time domain by inverse Fourier transform in the derivation of the speed of sound, so the calculation load can be lessened.

As described above, the ultrasonic diagnostic device 1 in this embodiment comprises transmitters (oscillators $24_1$ and $24_2$), the plurality of oscillators 24, the propagation path postulation component 41, the postulated propagation time calculator 42, the Fourier transform component 47, the phase shifter 48, and the sonic speed derivation component 51. The transmitters send ultrasonic waves toward the bone 10. The oscillators 24 receive the ultrasonic waves from the bone 10 and output received signals corresponding to the received ultrasonic waves. The propagation path postulation component 41 postulates the speed of sound through the bone 10, and calculates the propagation paths up until the ultrasonic waves sent out from the transmitters are received by the oscillators 24. The postulated propagation time calculator 42 calculates the propagation time it takes for the ultrasonic waves sent from the transmitters to be received by the oscillators 24, based on the propagation paths. The Fourier transform component 47 produces Fourier transform data by subjecting the I signals and Q signals outputted by the oscillators 24 to Fourier transform. The phase shifter 48 shifts the phase of the Fourier transform data for the oscillators 24 by frequency domain according to the propagation time. The sonic speed derivation component 51 determines the validity of the postulated speed of sound based on the Fourier transform data shifted by the phase shifter 48.

Processing to shift the phase of the signals that have been received can be performed by frequency domain by subjecting the signals to Fourier transform. With frequency domain, processing to shift the phase of the signals can be performed by simple computation, and almost no error occurs. Therefore, with the configuration of this embodiment, sonic speed derivation with good accuracy can be performed.

A preferred embodiment of the present invention was described above, but the above configuration can be modified as follows, for example.

In the above embodiment, the decimation processor 46 is configured to perform decimation of the signals before the Fourier transform is performed. However, the decimation may instead be performed after the Fourier transform and before the phase is shifted by the phase shifter 48. The decimation by frequency domain after Fourier transform can be implemented by deleting data in the high-frequency domain.

The IQ modulation, low-pass filtering, and decimation processing can also be omitted. That is, a first characteristic of the present invention is that the phases of signals are shifted and integrated in frequency domain, which prevents the occurrence of error when the signals are shifted. Therefore, processing such as IQ modulation is not necessarily required.

In the above embodiment, an ultrasonic wave beam was sent from the oscillators $24_1$ and $24_2$ toward the bone 10, and a surface refracted wave was generated. However, this is not the only option, and as shown in FIG. 1, etc., of Patent Literature 1, a dedicated transmitter for transmitting an ultrasonic wave beam toward the bone 10 may be separately provided to the oscillator array 22.

The ultrasonic diagnostic device 1 in the above embodiment was configured so that the computer 35 executed a sonic speed measurement program, thereby implementing various functions as a sonic speed measurement device. However, this is not the only option, and some or all of the functions as a sonic speed measurement device may be implemented by dedicated hardware. In particular, IQ modulation and low-pass filtering can also be performed directly on analog waveforms outputted by the oscillators 24. In this case, since I signals and Q signals with analog waveforms are produced, the reception circuit is configured to allow sampling of the I signals and the Q signals of the oscillators 24. Here, since the high frequencies are removed from the I signals and the Q signals by a low-pass filter, the sampling frequency in the reception circuit can be set low. In this case, the sampled I and Q signals will contain very little data from the outset, so decimation processing can be eliminated.

The method for evaluating the signal intensity of the integrated Fourier transform data ΣS is not limited to the above-mentioned intensity evaluation value V, and any method may be used. For example, the size of the spectrum of a particular angular frequency ω included in the integrated Fourier transform data ΣS can be used to evaluate the signal intensity, and the postulated speed of sound SOS when the spectrum of this particular angular frequency ω is at its largest can be employed as the measured value for the speed of sound.

The configuration of the present invention is not limited to an ultrasonic diagnostic device for displaying an echo image of bone, and can be widely utilized in devices in which the measurement object is something other than bone, such as an ultrasonic geological survey apparatus that uses ultrasonic waves to survey geological strata or underground structures. In particular, with the configuration of the above embodiment, the calculation load is reduced in derivation of the speed of sound, and the speed of sound can also be calculated in real time. Therefore, the present invention is expected to find application at sites where real-time calculation is important, such as seafloor geological surveys in which the speed of sound is measured during the movement of a ship.

Also, the signal transmitted by the propagation rate measurement device of the present invention is not limited to being an ultrasonic wave signal. The propagation rate measurement device of this embodiment can also be applied to geological stratum testing by low-frequency signal, or to non-destructive testing with electromagnetic waves, X-rays, or the like.

The invention claimed is:

1. A propagation rate measurement device comprising:
   a wave transmitter configured to transmit signals toward a measurement object;
   a plurality of receivers configured to receive signals from the measurement object, and configured to output received signals corresponding to the signals that have been received;
   a propagation path setting component configured to set propagation rate of signals through the measurement object, and configured to calculate propagation paths up until the signals transmitted from the wave transmitter are received by the receivers;
   a propagation time calculator configured to calculate propagation time it takes for the signals transmitted from the wave transmitter to be received by the receivers based on the propagation paths;
   a Fourier transform component configured to generate Fourier transform data by subjecting the received signals outputted by the receivers to Fourier transform;
   a phase shifter configured to shift phase of the Fourier transform data for the receivers by frequency domain according to the propagation time; and
   a propagation rate derivation component configured to determine validity of the set propagation rate based on the Fourier transform data that has been shifted by the phase shifter.

2. The propagation rate measurement device according to claim 1, further comprising
   an integration processor configured to calculate integrated Fourier transform data by integrating the Fourier transform data of the receivers whose phase has been shifted by the phase shifter by frequency domain,
   the propagation rate derivation component being further configured to determine the validity of the set propagation rate based on signal intensity of the integrated Fourier transform data.

3. The propagation rate measurement device according to claim 2, further comprising
   an IQ modulator configured to generate I signals and Q signals by IQ modulation of the signals received by the receivers, and
   a low-pass filter configured to cut out signals on a high frequency side of the I signals and the Q signals,
   the Fourier transform component being further configured to subject the I signals and the Q signals to the Fourier transform, and
   the phase shifter being further configured to shift phase of the I signals and the Q signals that have undergone the Fourier transform.

4. The propagation rate measurement device according to claim 3, further comprising
   a decimation processor configured to decimate the I signals and the Q signals.

5. The propagation rate measurement device according to claim 4, wherein
   the integration processor is further configured to integrate the I signals of the receivers that have undergone the Fourier transform and whose phase has been shifted, and the Q signals of the receivers that have undergone the Fourier transform and whose phase has been shifted by frequency domain.

6. The propagation rate measurement device according to claim 5, wherein
   the integration processor is further configured to multiply the I signals of the receivers that have undergone the Fourier transform and whose phase has been shifted, and the Q signals of the receivers that have undergone the Fourier transform and whose phase has been shifted by correction coefficients for correcting amplitude according to the receivers, respectively, and configured to integrate them.

7. The propagation rate measurement device according to claim 4, wherein the integration processor is further configured to multiply the I signals of the receivers that have undergone the Fourier transform and whose phase has been shifted, and the Q signals of the receivers that have undergone the Fourier transform and whose phase has been shifted by correction coefficients for correcting amplitude according to the receivers, respectively, and configured to integrate them.

8. The propagation rate measurement device according to claim 3, wherein
the integration processor is further configured to integrate the I signals of the receivers that have undergone the Fourier transform and whose phase has been shifted, and the Q signals of the receivers that have undergone the Fourier transform and whose phase has been shifted by frequency domain.

9. The propagation rate measurement device according to claim 8, wherein
the integration processor is further configured to multiply the I signals of the receivers that have undergone the Fourier transform and whose phase has been shifted, and the Q signals of the receivers that have undergone the Fourier transform and whose phase has been shifted by correction coefficients for correcting amplitude according to the receivers, respectively, and configured to integrate them.

10. The propagation rate measurement device according to claim 3, wherein
the integration processor is further configured to multiply the I signals of the receivers that have undergone the Fourier transform and whose phase has been shifted, and the Q signals of the receivers that have undergone the Fourier transform and whose phase has been shifted by correction coefficients for correcting amplitude according to the receivers, respectively, and configured to integrate them.

11. The propagation rate measurement device according to claim 2, wherein
the integration processor is further configured to multiply the I signals of the receivers that have undergone the Fourier transform and whose phase has been shifted, and the Q signals of the receivers that have undergone the Fourier transform and whose phase has been shifted by correction coefficients for correcting amplitude according to the receivers, respectively, and configured to integrate them.

12. A non-transitory computer readable medium recording a propagation rate measurement program that causes a computer to implement:

a received signal acquisition function of acquiring received signals from a plurality of receivers that is configured to receive signals transmitted from a wave transmitter toward a measurement object and returned from the measurement object and is configured to output the received signals corresponding to the signals that have been received;

a propagation path setting function of setting propagation rate of the signals through the measurement object, and calculating propagation paths up until the signals transmitted from the wave transmitter are received by the receivers;

a propagation time calculation function of calculating propagation time it takes for the signals transmitted from the wave transmitter to be received by the receivers based on the propagation paths;

a Fourier transform function of generating Fourier transform data by subjecting the received signals outputted by the receivers to Fourier transform;

a phase shift function of shifting phase of the Fourier transform data for the receivers by frequency domain according to the propagation time; and a propagation rate derivation function of determining validity of the set propagation rate based on the Fourier transform data that has been shifted by the phase shift function.

13. A propagation rate measurement method comprising:

acquiring received signals from a plurality of receivers that is configured to receive signals transmitted from a wave transmitter toward a measurement object and returned from the measurement object and is configured to output the received signals corresponding to the signals that have been received;

setting by a computer a propagation rate of the signals through the measurement object, and calculating propagation paths up until the signals transmitted from the wave transmitter are received by the receivers;

calculating propagation time it takes for the signals transmitted from the wave transmitter to be received by the receivers based on the propagation paths;

generating Fourier transform data by subjecting the received signals outputted by the receivers to Fourier transform;

shifting phase of the Fourier transform data for the receivers by frequency domain according to the propagation time; and determining validity of the set propagation rate based on the Fourier transform data that has been shifted.

* * * * *